United States Patent
Grodzins et al.

(10) Patent No.: US 6,442,233 B1
(45) Date of Patent: Aug. 27, 2002

(54) COHERENT X-RAY SCATTER INSPECTION SYSTEM WITH SIDESCATTER AND ENERGY-RESOLVED DETECTION

(75) Inventors: Lee Grodzins, Lexington, MA (US); William Adams, Powell, OH (US); Peter Rothschild, Newton, MA (US)

(73) Assignee: American Science and Engineering, Inc., Billerica, MA (US)

( * ) Notice: Subject to any disclaimer, the term of this patent is extended or adjusted under 35 U.S.C. 154(b) by 0 days.

(21) Appl. No.: 09/637,755

(22) Filed: Aug. 11, 2000

Related U.S. Application Data (63) Continuation-in-part of application No. 09/325,600, filed on Jun. 3, 1999, now abandoned.
(60) Provisional application No. 60/089,697, filed on Jun. 18, 1998.

(51) Int. Cl.[7] .................................. G01N 23/04
(52) U.S. Cl. ............................ 378/57; 378/70; 378/71; 378/86
(58) Field of Search ................... 378/51, 56, 57, 378/70, 71, 73, 86, 90, 207, 88

(56) References Cited

U.S. PATENT DOCUMENTS

| | | | | |
|---|---|---|---|---|
| 4,260,885 A | * | 4/1981 | Albert | 378/45 |
| 5,007,072 A | * | 4/1991 | Jenkins et al. | 378/88 |
| 5,491,738 A | * | 2/1996 | Blake et al. | 378/71 |
| 5,642,393 A | * | 6/1997 | Krug et al. | 378/57 |
| 5,682,412 A | * | 10/1997 | Skillicorn et al. | 378/98.6 |
| 5,696,806 A | * | 12/1997 | Grodzins et al. | 378/86 |
| 5,787,145 A | * | 7/1998 | Geus | 378/71 |
| 5,930,326 A | * | 7/1999 | Rothschild et al. | 378/57 |
| 6,118,850 A | * | 9/2000 | Mayo et al. | 378/83 |
| 6,192,101 B1 | * | 2/2001 | Grodzins | 378/55 |

* cited by examiner

Primary Examiner—Robert H. Kim
Assistant Examiner—Allen C. Ho
(74) Attorney, Agent, or Firm—Bromberg & Sunstein LLP (57) ABSTRACT

A system and method for inspecting an enclosure. A beam of x-rays is used for scanning the enclosure and for identifying areas of suspect material. The beam is subsequently coherently scattered off suspect materials, during the course of a single pass of the enclosure past the beam, for uniquely discriminating innocuous from contraband substances. One or more energy dispersive detectors measure radiation coherently scattered by an identified volume of suspect material. Absorption effects of the energy distribution of the coherently scattered radiation are compensated by means of a fiducial reference disposed between the interrogated object and the detectors.

28 Claims, 5 Drawing Sheets

COHERENT X-RAY SCATTER INSPECTION SYSTEM WITH SIDESCATTER AND ENERGY-RESOLVED DETECTION

This application is a continuation-in-part of application Ser. No. 09/325,600, filed Jun. 3, 1999, now abandoned, and claims priority from U.S. Provisional Application No. 60/089,697, filed Jun. 18, 1998, both of which applications are incorporated herein by reference.

TECHNICAL FIELD

The present invention relates to an x-ray system and method for identifying material within an obscuring enclosure, and more particularly to a system and method using coherently scattered penetrating radiation for discriminating target materials.

BACKGROUND OF THE INVENTION

The angular distribution of x-ray radiation scattered from a material when the radiation incident on the material is substantially monochromatic provides a well-established method for identifying the scattering material. The basis of the identifying characteristics of the scattered radiation is coherent x-ray scattering from the crystal planes of the bulk material. The well-known Bragg equation governs this so-called wavelength dispersive spectroscopy:

$$\sin\theta = n\lambda/(2d), \quad (1)$$

where d is the spacing between crystal planes, $\theta$ is the scattering angle, n is the order of scattering and $\lambda$ is the wave length of the radiation. Practitioners typically use low energy x-rays for these measurements, for example, the 8 keV (1.5 Å) x-rays from copper produce strong Bragg peaks at large, easily measured, scattering angles.

However, the identification of material in the interior of large containers typically employs radiation of higher energy. In particular, for luggage brought on board aircraft, typical x-ray energies are at least 75 keV, corresponding to a wavelength of ⅙th of an Angstrom. At this energy, the first Bragg peak (the closest to $\theta=0°$) will then be at a very small angle, typically in the range of a few degrees, making wavelength dispersive spectroscopy extremely difficult.

A more practical approach for the use of coherent scattering at higher energies, suggested by G. Harding and J. Kosanetzky, "Scattered X-Ray Beam Non-Destructive Testing," in Nuclear Instruments and Methods (1989), is to use energy dispersive spectroscopy. In energy dispersive spectroscopy, a polychromatic beam of high energy x-rays is sent through the container and the energy distribution at a fixed scattering angle of a few degrees is used to identify the object. The governing equation is the same as Eqn. 1, written to emphasize the energy dependence:

$$E = \frac{6.2}{d\sin\theta} \cong \frac{6.2}{d\theta}, \quad (2)$$

where d is the crystalline spacing in Angstroms, $\theta$ is the scattering angle in radians, and E is the x-ray energy in keV. Thus, for example, an x-ray of 100 keV will be Bragg scattered through an angle of about 2° by a crystalline substance with spacings of about 2 Å.

Bragg-scattering inspection systems under current development seek to examine the entire volume of every piece of luggage that enters an aircraft. The hardware to carry out this daunting task is complex and expensive, and are at least 2 orders of magnitude too slow to be effective as a screener at an airport terminal.

Additionally, since the Bragg scattering angles are so low (typically 2°–30°), the collimation requirements on the detector are stringent if a particular volume along the x-ray path into the interrogated volume is to be discriminated. The strict requirement on the collimation of the coherent-scatter detector can be quantified by noting that an uncertainty in the angle results in an uncertainty in the measured energy. Differentiating Equation (2) gives the necessary relation:

$$\frac{\Delta E}{E} \cong -\frac{\Delta\theta}{\theta}. \quad (3)$$

To obtain a full-width energy resolution of $\Delta E/E=5\%$, the angular uncertainty $\Delta\theta/\theta$ must be kept to 5%. (A 5% uncertainty is typical of the maximum uncertainty that can be tolerated if the coherent scatter method is to effectively discriminate between different types of materials.) The collimation must therefore be good enough to limit the acceptance angle to 2° with an accuracy of 5%, a difficult requirement.

The small scattering angles with their tight uncertainty requirements severely restrict the length along the beam that can be inspected by a single coherent-scatter detector, typically to no more than 3 cm. If the position along the beam path of a suspect volume of an inspected enclosure is unknown, then it becomes necessary to make 5 to 10 separate measurements (or, alternatively, to provide the same number of carefully collimated detector elements) to inspect all the voxels along a given beam path. In one case, inspection times are increased, and in the other, the cost of the system is impacted substantially.

SUMMARY OF THE INVENTION

In accordance with one aspect of the invention, in a preferred embodiment, there is provided an inspection system for inspecting an enclosure. The system has a source for producing a pencil beam of penetrating radiation and a substantially inertia-free scanner for scanning the beam through successive positions with respect to the enclosure. The system has at least one detector for generating a signal based on at least one of penetrating radiation transmitted through the enclosure and penetrating radiation scattered by the enclosure, a processor for identifying positions warranting scrutiny on the basis of the signal from the at least one detector and a set of specified conditions, and at least one Bragg detector for determining a spectrum of coherent scattering from an identified volume within the enclosure. In accordance with alternate embodiments of the invention, the at least one Bragg detector may be a multi-element solid-state detector. The system may also include a fiducial material disposed in the beam posterior to the enclosure with respect to the source for correcting spectral distortions due to wavelength-dependent absorption of the beam of penetrating radiation.

In a preferred embodiment, the scanner may have a beam control arrangement for scanning a position of an electron beam with respect to an x-ray emissive anode and a perforated absorbing shield for permitting emission of penetrating radiation at a single emission angle determined by the position of the electron beam. The beam control arrangement may include at least one of a magnetic control yoke and an array of electrical deflector plates. In accordance with other embodiments of the invention, the scanner may include a mechanically positionable aperture, and the inspection system may also include a translator for positioning the at least one Bragg detector in response to identification by the processor of positions warranting scrutiny.

In accordance with one aspect of the invention, in one of its embodiments, there is provided an inspection system for inspecting an enclosure. The system has a source for producing a beam of penetrating radiation and a scanner for scanning the beam through successive positions with respect to the enclosure. The inspection system has a set of detectors disposed along a direction substantially parallel to the beam, the set of detectors generating a sidescatter signal based on penetrating radiation sidescattered by the object, and a controller for identifying a position of a suspected object based at least in part upon the sidescatter signal. Additionally, the inspection system has at least one Bragg detector for determining a spectrum of coherent scattering from the position of the suspected object.

In accordance with alternate embodiments of the invention, the beam of penetrating radiation may have a specified beam profile, more particularly, that of a pencil beam. The beam of penetrating radiation may be an x-ray beam. Each Bragg detector may be a multi-element solid-state detector and may be energy-dispersive. The inspection system may also include a fiducial material disposed in the beam posterior to the enclosure with respect to the source for correcting spectral distortions due to wavelength-dependent absorption of the beam of penetrating radiation.

In accordance with further embodiments of the invention, an inspection system is provided for characterizing the nature and three-dimensional position of an object contained within an enclosure. In addition to a source for producing a beam of penetrating radiation and a scanner for scanning the beam through successive positions with respect to the enclosure, the system has a set of detectors disposed along a direction substantially parallel to the beam, the set of detectors generating a sidescatter signal based on penetrating radiation sidescattered by the object. The system also has a controller for identifying a position of a suspected object based at least in part upon the sidescatter signal and a plurality of Bragg detectors disposed along a direction substantially transverse to the beam for measuring an angular distribution of coherently scattered penetrating radiation.

In accordance with a further aspect of the present invention in one of its embodiments, there is provided a method for inspecting an enclosure. The method has the steps of:
   a. producing a pencil beam of penetrating radiation;
   b. scanning the beam through successive positions with respect to the enclosure;
   c. detecting with an x-ray detector at least one of penetrating radiation transmitted through the enclosure and penetrating radiation scattered by the enclosure;
   d. identifying positions warranting scrutiny on the detected penetrating radiation; and
   e. determining a spectrum of coherent scattering from an identified volume within the enclosure during the course of a single pass of the enclosure past the beam.

The method may also have a step of determining a spectrum of coherent scattering from a reference material disposed within the beam at a position posterior to the enclosure with respect to the source. Additionally, the method may have the steps of determining spectra of coherent scattering from a plurality of volumes within the enclosure and including positioning a reference material between each of the plurality of volumes and the x-ray detector.

BRIEF DESCRIPTION OF THE DRAWINGS

The foregoing features of the invention will be more readily understood by reference to the following detailed description taken with the accompanying drawings in which.

DETAILED DESCRIPTION OF PREFERRED EMBODIMENTS

Figure 1:
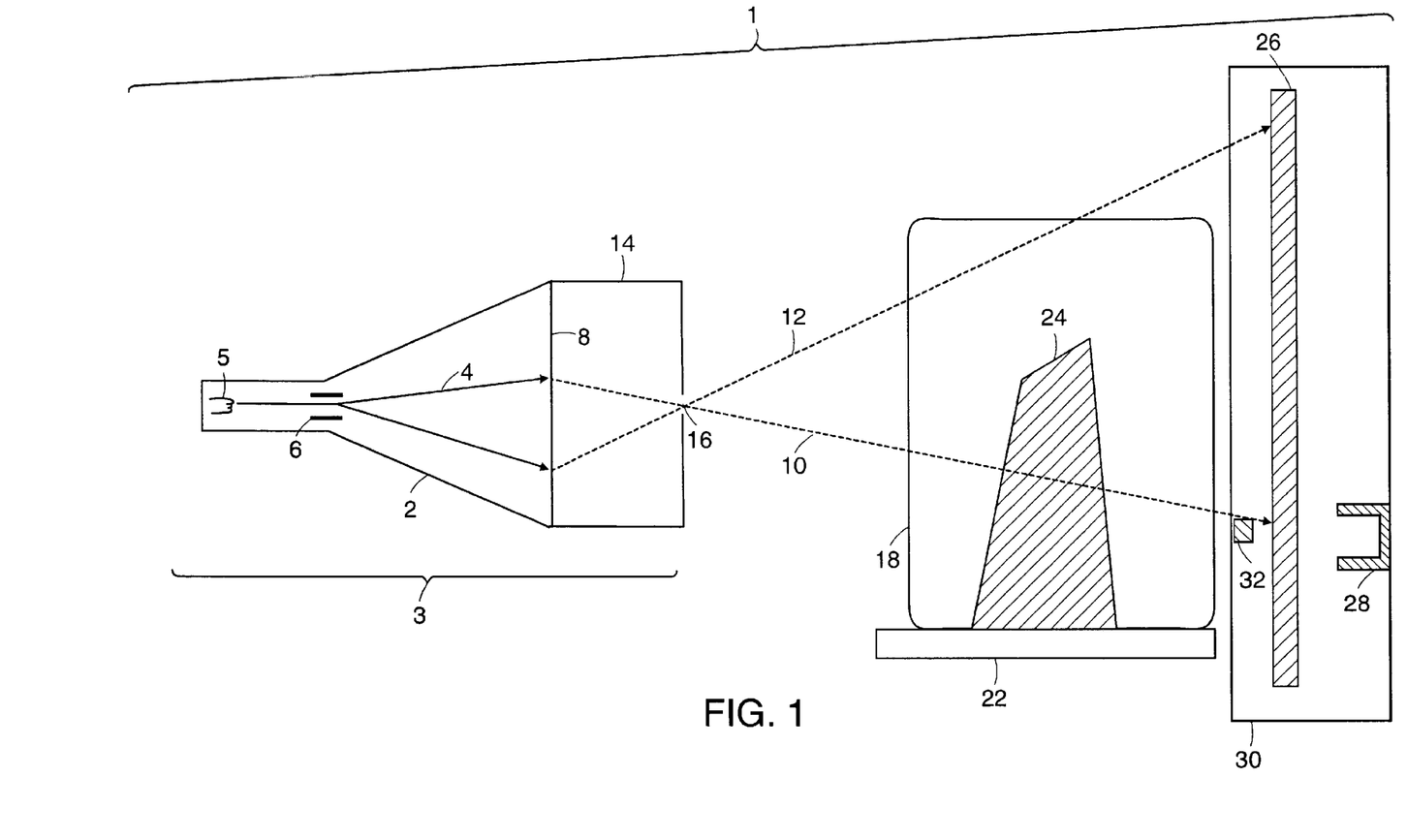
FIG. 1 is a schematic elevation view of an x-ray inspection system in accordance with an embodiment of the present invention.

Referring to FIG. 1, an elevation view is shown of an x-ray inspection system in accordance with a preferred embodiment of the invention, the inspection system designated generally by numeral 1. A source 2 of penetrating radiation produces a beam 10 of penetrating radiation such as x-rays. Beam 10 has a prescribed cross sectional profile, typically that of a flying spot or pencil beam. Beam 10 will be referred to in the present description, without limitation, as an x-ray beam, and also, without limitation, as a pencil beam. In a preferred embodiment of the invention, a scanned pencil beam, whose position and cross section is well known at every point in time, is used. The cross section of the pencil beam defines the spatial resolution of the images. Typical pencil beam sizes are a few mm in diameter at a distance of a meter from the beam defining collimation; that is, an angular spread in the beam of <5 milliradians. Thus, the beam widths are more than a factor of 10 smaller than the scattering angles of 2° to 3° that are desired for Bragg measurements of penetrating x-rays.

Various scanning systems 3 are known to persons skilled in the art to provide for scanning of beam 10 across a region of space which may include a target container (or enclosure) 18 the contents of which are to be scrutinized. In accordance with a preferred embodiment of the invention, scanning system 3 may include a controlled electron beam 4 emanating from cathode 5, which electron beam 4 is scanned, using standard electron beam control elements such as electrical deflector plates 6 or a magnetic control yoke (not shown), over an x-ray emissive anode 8. A hole 16 in absorbing shield 14 disposed on the side of anode 8 opposite electron beam 4, produces a beam 10 of x-rays that scans across the target container 18 as the electron beam 4 sweeps over anode 8. Container 18 may be any enclosure, and is shown for heuristic purposes to illustrate typical applications, however in an alternate embodiment of the invention, the invention may be practiced without the enclosure. The absorbing shield 14 may have a single hole 16 so that the beam 10 scans a volume, triangular in cross section, with hole 16 at the apex, or, alternatively, shield 14 may have a series of in-line holes, as described in copending U.S. patent application Ser. No. 09/599,386, which is incorporated herein by reference. By using a series or array of in-line holes, beam 10 may be emitted in approximately perpendicular to anode 8 with successive x-ray beams being approximately parallel to each other.

Container 18 with object 24 representative of the unknown contents of the container, may be conveyed through the x-ray beam 10 such as by a conveyor 22, for example. X-rays transmitted through container 18 are detected in x-ray detector 26. Additionally, a Bragg scattering detector array 28 and a reference crystal 32, both of which are discussed in further detail below, may be positionable, as by mechanical translation, along track 30 using ordinary positioning methods. This allows scattering detector array 28 and a reference crystal 32 to be positioned for measurements of a given x-ray beam trajectory.

In a preferred embodiment, scanning system 3, in accordance with the embodiment depicted in FIG. 1, uses an arrangement for control of electron beam 4 similar to that of a cathode ray tube or television tube and can respond rapidly to vary the scan speed or cause the electron beam, and hence the x-ray beam, to dwell at a specific point. The x-ray scan of the container 18 may be caused to proceed at the rate that gives the most effective information about the contents of container 18. Information about the effective atomic number of objects in the container may be obtained from the transmitted radiation and from scattered radiation, such as backscattered radiation, as known to persons skilled in the art, and the use of detectors of scattered radiation, while not shown, is within the scope of the present invention and of the appended claims.

If the x-ray inspection, as heretofore described, detects that a specific volume of container 18 might contain contraband material or other material warranting more detailed scrutiny, the electron beam 4 may be automatically positioned so that the x-ray pencil beam 10 passes through the suspect volume. Bragg scatter detector array 28 consists of a linear or areal array of energy dispersive detectors such as CdZnTe. Each detector is collimated so that it is sensitive only to x-rays scattered through a specific narrow range of angles from a specific depth in the container. The Bragg detector array 28, as well as reference material 32, is normally out of the beam. When examining a suspect volume of container 18, the array and reference material are positioned appropriately so as to determine the Bragg scatter intensity pattern from each of the volume elements along the x-ray beam path.

Figure 2A:
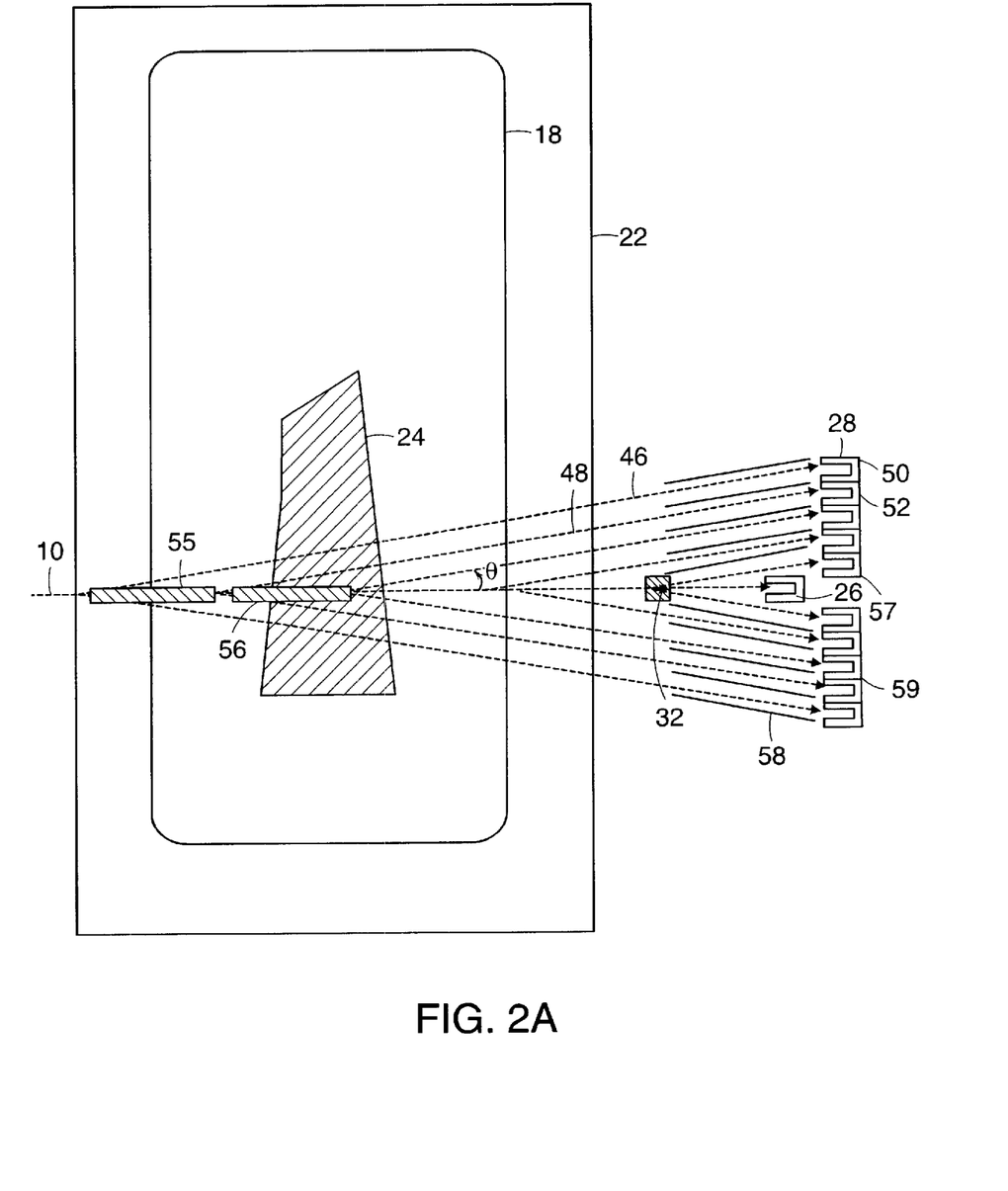
FIG. 2A is a schematic plan view of the x-ray inspection system of FIG. 1 showing an x-ray beam traversing an inspected enclosure and a Bragg scattering identification apparatus.

Referring to FIG. 2A, a top view of the inspection system of FIG. 1 is shown in cross-section. X-ray beam 10 passes through the container 18 and is detected in detector 26. Additionally, an array 28 of detectors 50, 52, and 57 are arranged on either side of beam 10. Each detector 50 has collimators 58 so that each detector 50 is sensitive only to x-rays scattered from a specified depth in the container 18 and through a specified range of small angles. Thus detector 50 detects x-rays from the line path 46 that are scattered from volume 55 through an angle $\theta$, while detector 52 detects x-rays from the line path 48 that are scattered from volume 56 through similar angle $\theta$. Array 28 of detectors covers the full width of the containers 18. The mirror set of detectors 59 on the opposing side of beam 10 is also shown.

Each Bragg detector 50 may be an energy dispersive, multi-element solid state detector. Bragg detector 50 may be a ring detector and the detectors may constitute a nested set of multiple ring detectors and may be moved to line up with the beam and measure the x-rays scattered into a specified angle.

A problem with energy-dispersive Bragg scattering is that beam hardening due to intervening absorption of x-ray radiation within container 18 strongly reduces the low energy peaks relative to the higher energy peaks. Thus the signature of a target compound such as an explosive or drug may be distorted. To correct for that distortion, in accordance with the present invention, a fiducial material 32 is rotated in and out of x-ray beam path 10. Fiducial material 32 may be a reference crystal and is selected so that the scattering peaks of fiducial material 32 preferably lie outside the peaks that identify the sought for material. If the peaks are truly distinct then the fiducial material may also be in the scatter path always. The fiducial peak intensities, without absorption are independently measured and stored. The intensities measured with the luggage in place are then corrected according to the ratio of the measured to stored values and these ratios are used to determine the absorption versus x-ray energy curve that is used to correct the intensity of the energy peaks caused by the material in the examined container. X-rays that are Bragg scattered from reference object 32 are detected in 57. Reference object 32 produces a spectrum in detector 57 that has been distorted by the absorption of x-ray beam 10 as it passes through container 18. Comparing the observed spectrum with the spectrum produced without any intervening absorbing material gives a first order correction for the absorption of all of the Bragg scattered beams since all of the Bragg scatterings are through small angles and the total absorption correction for the scattered beams 46 and 48 will be close to that of primary beam 10. It should be noted however, that the extension to placing reference crystals in each path is straightforward but does involve additional detectors for measuring the Bragg scattering from the each reference block.

In another preferred embodiment, inspection of container 18 may be carried out in a single pass. The time required to determine the crystalline nature of specific object is typically a fraction of a second so that the examination of as many as ten suspect areas may add no more than an extra second or two to the examination. Such an examination modality advantageously employs the inertia-free character of electronic control of the beam direction, in accordance with the description provided above with reference to FIG. 1.

Figure 2B:
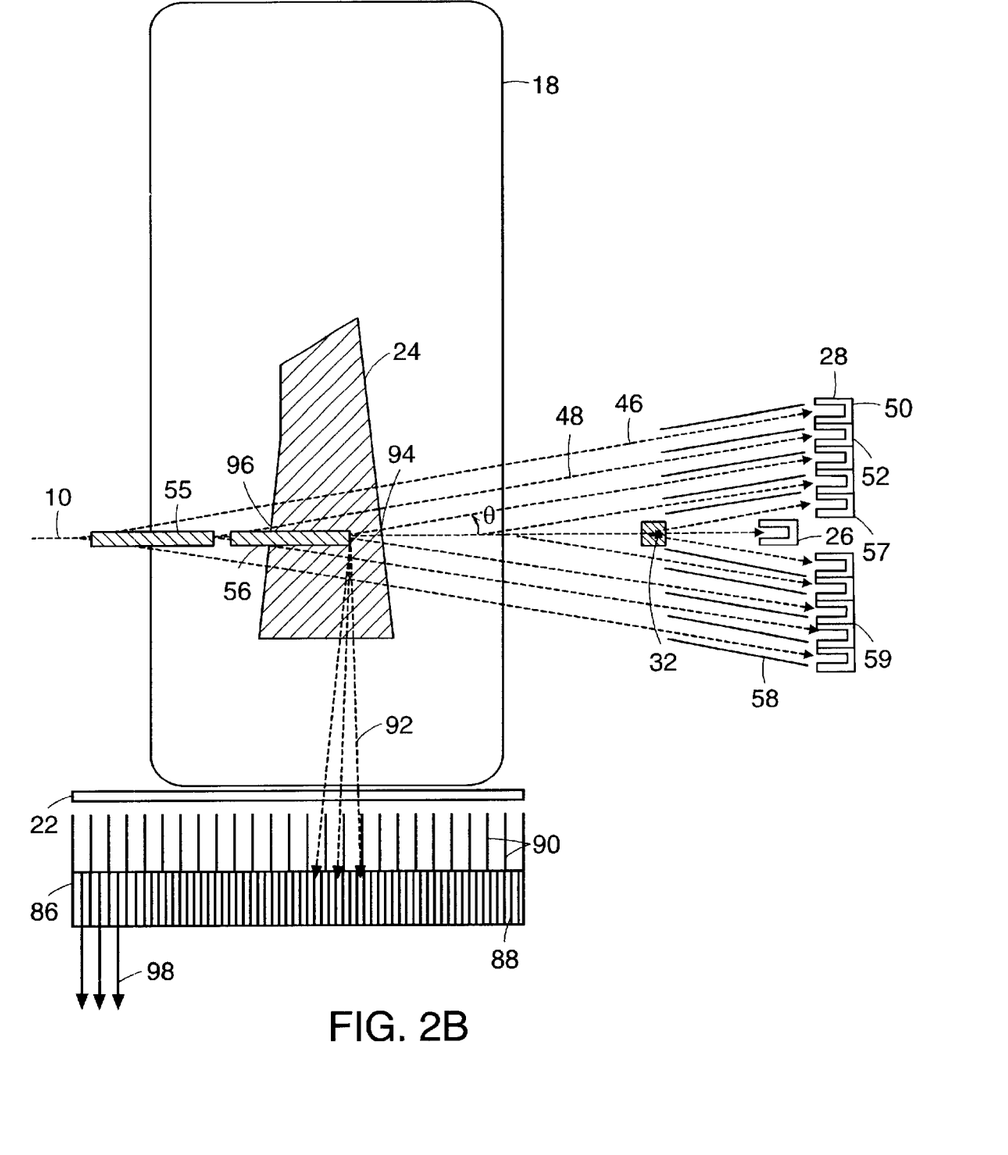
FIG. 2B is a schematic elevation view of an x-ray inspection system in accordance with alternate embodiments of the invention, in which both Bragg and Compton scattering identification apparatus is employed.

Referring to FIG. 2B, an elevation view is shown of an alternate embodiment of the invention. As in FIG. 2, enclosure 18 scanned by penetrating beam 10 as it is conveyed on conveyor 22. In order to scrutinize the material comprising a volume of container 18 on the basis of the Bragg scatter detected at Bragg scatter detector array 28, it is desirable to resolve the ambiguity as to where along the path of penetrating beam 10 the scatter is arising without recourse to collimators 58. This is because Bragg scattering angles are typically so low (2–3°) that the resolution achievable by means of collimators 58 is severely constrained. In accordance with various embodiments of the invention, one or more arrays 86 of side-scatter detectors 88 is used for locating the position of a suspect object along the x-ray path 10. Techniques for employing side-scatter detectors to determine edges and material characteristics of an object are described, for example, in Grodzins et al. (U.S. Pat. No. 5,696,806, issued Dec. 9, 1997) and Rothschild et al. (U.S. Pat. No. 5,930,326, issued Jul. 27, 1999), both of which patents are incorporated herein by reference. As shown in FIG. 2B, collimators 90 limit the field-of-view of each segment 88 of segmented side-scatter detector array 86 such that, given the direction of beam 10, the volume element 56 giving rise to detected Compton scattering 92 may be identified. Moreover, in accordance with the teachings of the patents incorporated by reference, the leading and trailing edges 94 and 96 of a concealed object 24 in the slice subtended by beam 10 maybe identified. Thus the range of angles $\theta$ giving rise to Coherent scattering at Bragg array 28 may be independently determined and Eqn. 1 may be applied. As taught in Rothschild et al., fiber optic links 98 may be provided to convey scintillation light to photomultipliers (not shown).

It should be emphasized that the sidescatter techniques described herein may provide two independent advances over transmission scanning for identifying suspect volumes for scrutiny by coherent scattering. First, the sidescatter technique produces a measure of the density of objects which may supplement measures of atomic number obtained by transmission or backscatter techniques. Sidescatter techniques may thus advantageously result in fewer false alarms, requiring fewer volume elements requiring follow-up inspection by coherent scattering. Second, sidescatter techniques may pinpiont a specific volume element along the beam path so that coeherent scattering may be carried out with a single detector, or, at most, a detector with a small number of detector elements, rather than by a complex and costly hodoscope of energy-dispersive detectors. Times for a full inspection may be reduced by more than a factor of two.

In accordance with yet other embodiments of the invention, both angular and energy distributions of the Bragg-scattered x-ray beam are measured simultaneously. Thus, a given source of coherent scattering provides a photon of energy multiplex advantage since count rates are increased, all angles of interest being recorded simultaneously. Thus, a given source of coherent scatter provides a photon of energy $E_1$ into a detector at scatter angle $\theta_1$), and, simultaneously, a photon of energy $E_2$ into a detector at scatter angle $\theta_2$, both photons obeying Eqn. 2, and thereby allowing crystal spacing d to be determined with increased signal-to-noise relative to systems wherein only the angular distribution is measured for a monochromatic beam, or only the energy spectrum is measured at a fixed angle. As apparent from Eqn. 2, the crystal spacing d is directly proportional to the product of x-ray energy E and scattering angle $\theta$, and thus a given spacing is readily recognized as a hyperbola in the E-$\theta$ plane.

Figure 3:
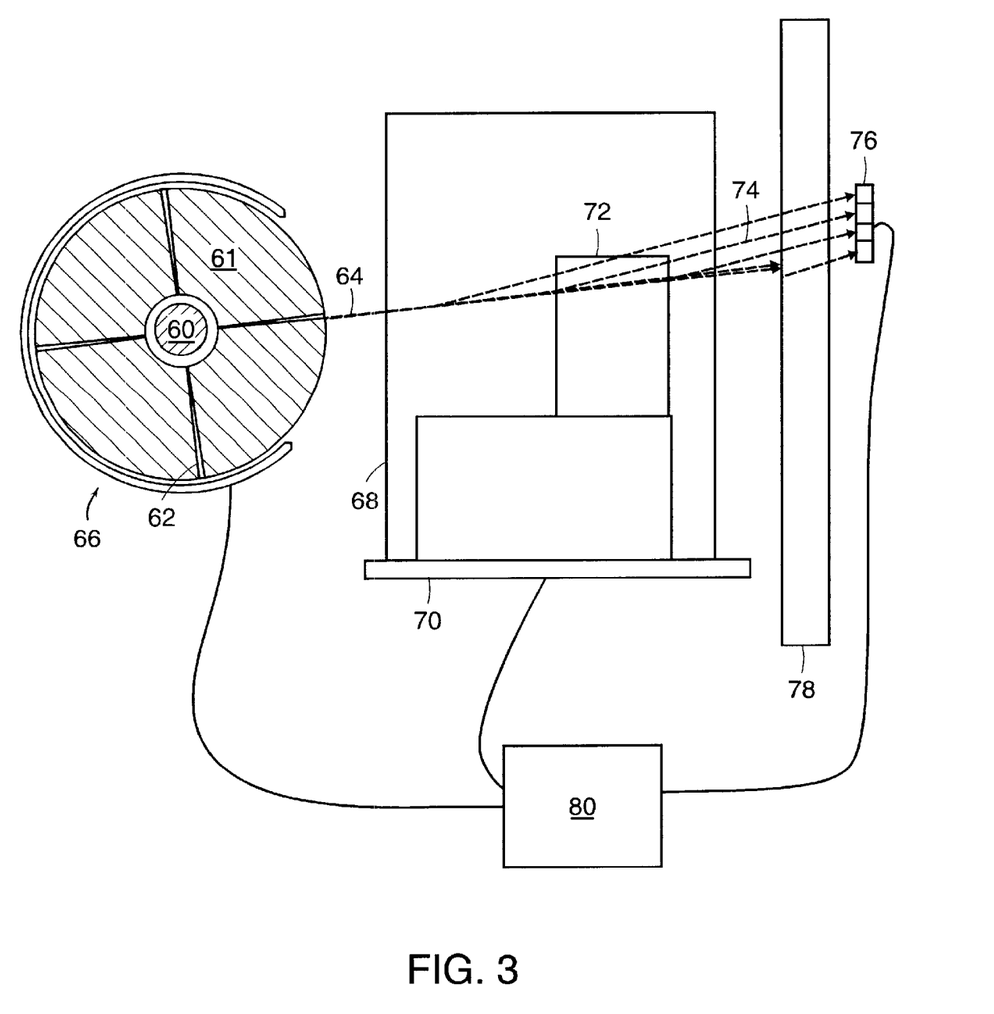
FIG. 3 is an elevation schematic of the scanning carried out with a mechanical scanner in accordance with an alternate embodiment of the present invention.
Figure 4:
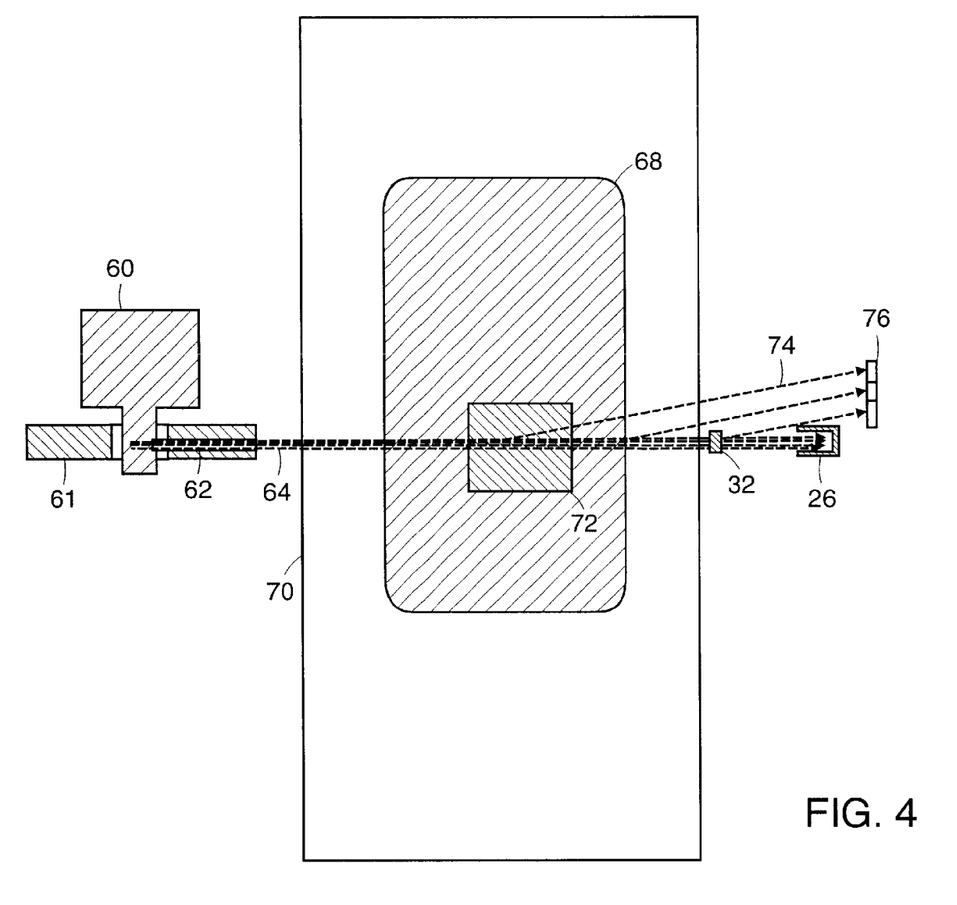
FIG. 4 is a plan schematic of the mechanically scanned inspection system of FIG. 3.

FIGS. 3 and 4 show elevation and plan views, respectively, of an x-ray inspection system in accordance with an alternate embodiment of the present invention. Referring to FIG. 3, an x-ray tube 60 is in the center of a mechanical scanner 66 which includes a rotating wheel 61 of material substantially opaque to x-rays but for hollow spokes 62. X-ray beams 64 sweep in the plane of the drawing over a container 68 and the transmitted x-rays are detected in detector 78. An image of the transmitted x-ray intensities is obtained as container 68 is conveyed through the rastered x-rays by the conveyor 70. A Bragg scatter detector array 76, displaced from the plane of the x-ray beam, detects the scattered radiation 74.

Referring to FIG. 4, the inertia of the mechanical scanner 66 does not allow it to be stopped quickly. When mechanical scanner 66 is used, the screening inspection is completed and specific areas of suspect materials are entered into the computer 80 that controls the digitally driven components: conveyor 70, rotating wheel 61, and the position of the Bragg detector 76 together with reference material 32. Each component is placed in precise registration for Bragg scatter inspection. Container 68 is then brought back into x-ray beam 64 and the specific suspect areas 72 are examined automatically in sequence.

By combining the screening and the verifier in a single unit, with one x-ray source, it becomes practical to make an economical scanning system that may provide high throughput, high detection efficiency and a very low false alarm rate. Increased speed of inspection may be obtained since scrutiny by a Bragg detector is reserved for only those portions of the enclosure which are suspected on the basis of inspection by other means.

The described embodiments of the invention are intended to be merely exemplary and numerous variations and modifications will be apparent to those skilled in the art. All such variations and modifications are intended to be within the scope of the present invention as defined in the appended claims.

We claim:

1. An inspection system for inspecting an enclosure, the system comprising:

a. a source for producing a pencil beam of penetrating radiation;

b. a substantially inertia-free scanner for scanning the pencil beam through successive positions with respect to the enclosure;

c. at least one detector for generating a signal based on at least one of penetrating radiation transmitted through the enclosure and penetrating radiation scattered by the enclosure;

d. a processor for identifying positions warranting scrutiny on the basis of the signal from the at least one detector and a set of specified conditions;

e. at least one Bragg detector for determining an energy spectrum as a function of angular distribution of coherent scattering of the pencil beam from an identified volume within the enclosure; and f. a controller for determining a crystal spacing of the suspected object from the angular distribution of the energy spectrum of the coherent scattering.

2. An inspection system according to claim 1, wherein the beam of penetrating radiation is an x-ray beam.

3. An inspection system according to claim 1, wherein the at least one Bragg detector is a multi-element solid-state detector.

4. An inspection system according to claim 1, wherein the at least one Bragg detector is an energy dispersive detector.

5. An inspection system according to claim 1, further including a fiducial material disposed in the beam posterior to the enclosure with respect to the source for correcting spectral distortions due to wavelength-dependent absorption of the beam of penetrating radiation.

6. An inspection system according to claim 1, further including a fiducial material interposed in the beam between the enclosure and at least one of the at least one detector for correcting spectral distortions due to wavelength-dependent absorption of the beam of penetrating radiation.

7. An inspection system according to claim 1, wherein the scanner comprises:

a. an electron beam deflector for scanning a position of an electron beam with respect to an x-ray emissive anode; and b. a perforated absorbing shield disposed between the x-ray emissive anode and the enclosure for permitting emission of penetrating radiation at a single emission angle determined by the position of the electron beam.

8. An inspection system according to claim 7, wherein the scanner is configured such that a beam of x-rays is emitted in a direction substantially perpendicular to the anode.

9. An inspection system according to claim 7 wherein the electron beam deflector includes at least one of a magnetic control yoke and an array of electrical deflector plates.

10. An inspection system according to claim 1, further including a translator for positioning the at least one Bragg detector in response to identification by the processor of positions meeting a specified criterion for scrutiny.

11. An inspection system for characterizing an object contained within an enclosure, the system comprising:
   a. a source for producing a beam of penetrating radiation;
   b. a scanner for scanning the beam through successive positions with respect to the enclosure;
   c. a set of detectors disposed along a direction substantially parallel to the beam, the set of detectors generating a sidescatter signal based on penetrating radiation sidescattered by the object;
   d. a controller for identifying a position of a suspected object based at least in part upon the sidescatter signal;
   e. at least one Bragg detector for measuring an energy spectrum of coherent scattering as a function of angular distribution from the position of the suspected object; and
   f. a controller for determining a crystal spacing of the suspected object from the angular distribution of the energy spectrum of the coherent scattering.

12. An inspection system according to claim 11, wherein the beam of penetrating radiation has a specified beam profile.

13. An inspection system according to claim 11, wherein the beam of penetrating radiation is a pencil beam.

14. An inspection system according to claim 11, wherein the beam of penetrating radiation is an x-ray beam.

15. An inspection system according to claim 1, wherein the at least one Bragg detector is a multi-element solid-state detector.

16. An inspection system according to claim 11, wherein the at least one Bragg detector is an energy-dispersive detector.

17. An inspection system according to claim 11, further including a fiducial material disposed in the beam posterior to the enclosure with respect to the source for correcting spectral distortions due to wavelength-dependent absorption of the beam of penetrating radiation.

18. An inspection system according to claim 11, further including a fiducial material interposed in the beam between the enclosure and at least one of the at least one detector for correcting spectral distortions due to wavelength-dependent absorption of the beam of penetrating radiation.

19. An inspection system according to claim 11, wherein the scanner comprises:
   a. an electron beam deflector for scanning a position of an electron beam with respect to an x-ray emissive anode; and
   b. a perforated absorbing shield disposed between the x-ray emissive anode and the enclosure for permitting emission of penetrating radiation at a single emission angle determined by the position of the electron beam.

20. An inspection system for characterizing an object contained within an enclosure, the system comprising:
   a. a source for producing a beam of penetrating radiation,
   b. a scanner for scanning the beam through successive positions with respect to the enclosure;
   c. a set of detectors disposed along a direction substantially parallel to the beam, the set of detectors generating a sidescatter signal based on penetrating radiation sidescattered by the object;
   d. a controller for identifying a position of a suspected object based at least in part upon the sidescatter signal; and
   e. a plurality of Bragg detectors disposed along a direction substantially transverse to the beam for measuring an angular distribution of coherently scattered penetrating radiation.

21. An inspection system according to claim 20, wherein the beam of penetrating radiation is monochromatic.

22. An inspection system according to claim 20, wherein at least one of the plurality of Bragg detectors is energy dispersive.

23. A method for inspecting an enclosure, the method comprising:
   a. producing a beam of penetrating radiation;
   b. scanning the beam through successive positions with respect to the enclosure;
   c. detecting with an x-ray detector at least one of penetrating radiation transmitted through the enclosure and penetrating radiation scattered by the enclosure;
   d. identifying positions warranting scrutiny of the detected penetrating radiation; and
   e. determining an energy spectrum of coherent scattering as a function of angular distribution from an identified volume within the enclosure during the course of a single pass of the enclosure past the beam of penetrating radiation.

24. A method according to claim 23, further including the step of determining an energy spectrum of coherent scattering from a reference material disposed within the beam at a position posterior to the enclosure with respect to the source.

25. A method according to claim 23, further including the step of determining energy spectra of coherent scattering from a plurality of volumes within the enclosure.

26. A method according to claim 25, further including positioning a reference material between each of the plurality of volumes and the x-ray detector.

27. A method according to claim 23, further including:
   f. determining the crystal spacing of the suspected object from the energy spectrum of coherent scattering as a function of angular distribution.

28. A method according to claim 27, further including the step of determining a spectrum of coherent scattering from a reference material disposed within the beam at a position posterior to the enclosure with respect to the source.

* * * * *